United States Patent [19]

Berry et al.

[11] Patent Number: 4,899,356
[45] Date of Patent: Feb. 6, 1990

[54] METHOD OF RADIOGRAPHIC INSPECTION OF WOODEN MEMBERS

[75] Inventors: Maggie L. Berry; Robert F. Berry, Jr., both of Hayes, Va.

[73] Assignee: The United States of America as represented by the Administrator of the National Aeronautics and Space Administration, Washington, D.C.

[21] Appl. No.: 125,678

[22] Filed: Nov. 25, 1987

[51] Int. Cl.⁴ ............................................. G01B 15/06
[52] U.S. Cl. ........................................ 378/58; 378/51
[58] Field of Search ....................... 378/57, 58, 62, 51; 250/302

[56] References Cited

U.S. PATENT DOCUMENTS

| | | | |
|---|---|---|---|
| 2,516,857 | 5/1947 | Forest et al. | 250/302 |
| 3,279,243 | 10/1966 | Molina | 250/302 |
| 3,704,370 | 11/1972 | Shelton | 378/58 |
| 3,764,811 | 10/1973 | Lange | 250/302 |
| 3,899,450 | 8/1975 | Molina | 250/302 |
| 3,904,545 | 9/1975 | Molina | 250/302 |
| 4,172,224 | 10/1979 | Lapinski et al. | 378/58 |

FOREIGN PATENT DOCUMENTS 0223534  6/1985  Fed. Rep. of Germany ........ 378/58

Primary Examiner—Craig E. Church
Attorney, Agent, or Firm—Harold W. Adams; John R. Manning; Charles E. B. Glenn

[57] ABSTRACT

The invention is a method of radiographic inspection of a wooden specimen 11 for internal defects which includes the steps of introducing a radiopaque penetrant into any internal defects in said specimen 11 through surface openings therein; passing a beam of radiation through a portion of the specimen to be inspected; and making a radiographic film image of the radiation passing through said specimen, the radiopaque penetrant in said specimen absorbing a portion of said radiation passing therethrough, thereby enhancing the resulting image of said internal defects in said specimen 11.

4 Claims, 2 Drawing Sheets

METHOD OF RADIOGRAPHIC INSPECTION OF WOODEN MEMBERS

ORIGIN OF THE INVENTION

The invention described herein was made by employees of the U.S. Government and may be manufactured and used by or for the Government for governmental purposes without the payment of any royalties thereon or therefor.

BACKGROUND OF THE INVENTION

1. Field of the Invention

The invention relates to a method of radiographic inspection of wooden members and more particularly to the use of a radiopaque penetrant in the member inspected to visually enhance the contrast of the image of any internal defects with the image of other properties therein on a radiographic film.

2. Description of the Prior Art

Radiopaque penetrants have been used to improve the contrast of radiographic film image of defects in materials of substantially uniform density and internal formation such as bronze, brass, other metals, plastic and rubber. Even in these relatively homogeneous materials, the use of known penetrants may be restricted because of their extremely low toxicity threshold limit value (TLV). For instance, s-tetrabromoethane ($C_2H_2Br_4$), a commercially available penetrant, has a toxicity TLV of only one part per million, making it extremely hazardous to use for radiographic purposes. Another radiopaque penetrant, a solution of zinc iodide crystals ($ZnI_2$) in water and isopropyl alcohol, poses little health problem, but its use may lead to contamination of the member inspected by local staining and discoloration caused by residual $ZnI_2$ crystals.

OBJECTS AND SUMMARY OF THE INVENTION

An object of the invention is to provide a method of radiographic inspection of wood members using a radiopaque penetrant.

The above and numerous other objects and advantages are achieved in accordance with the method of this invention which includes the steps of introducing a radiopaque penetrant into internal defects in a wooden specimen to be inspected through a surface opening therein; subjecting the specimen to sufficient radiation to pass through said wooden specimen: and making a radiographic film image of said radiation passing through said wooden specimen, the radiopaque penetrant in the internal defects within said wooden specimen absorbing a portion of said radiation passing therethrough thereby enhancing the resulting film image of the internal defects.

A radiographic film image of the selected site of the specimen may first be made before introducing the radiopaque penetrant into the specimen and the "before" and "after" radiographic film images compared.

BRIEF DESCRIPTION OF THE DRAWINGS

The above and numerous other objects and advantages may be achieved in practicing the invention will become apparent from the following detailed description when read in view of the appended drawings wherein.

BRIEF DESCRIPTION OF THE INVENTION

The inhomogeneity of many woods results from changes in the form of both early wood and late wood growth, grain structure, moisture, knot holes, density, porosity and other internal variations which selectively and variably attenuate or absorb the radiation of any x-rays used in a radiograph inspection of wooden specimens. This makes the resulting radiographic film images difficult to interpret, even in the absence of de-laminations, cracks, voids or other internal defects that extend to the surface, the images of which are superimposed on the normal and already difficult to interpret radiographic film images.

In accordance with this invention, the suspected internal defect strata in a wooden specimen, which may be revealed by external surface signs such as cracks, splits and voids, is filled with a radiopaque penetrant such as ($CCL_2FCCLF_2$), commercially known as Freon TF, made by E. I. DuPont, Inc., Wilmington, Del., a readily available fluorocarbon cleaning solvent. This is accomplished by flooding the external surface area with sufficient penetrant to fill the internal defects in the wooden specimen.

The Freon TF has a molecular weight of 187.39, a favorable toxicity threshold limit value of 1000 parts per million, and an evaporation rate of 170 (that of carbon tetrachloride is 100), and leaves no residue to stain or discolor the wooden specimens. Its radiation absorption qualities are sufficient to practice the method even in inspecting wooden specimens up to twenty-eight (28) inches in thickness, which has been successfully accomplished. In using Freon TF as a penetrant, reasonable rather than extremely stringent safety precautions are required for ventilation and handling. Ready availability permits its widespread use as a radiopaque penetrant in accordance with the invention.

Figure 1:
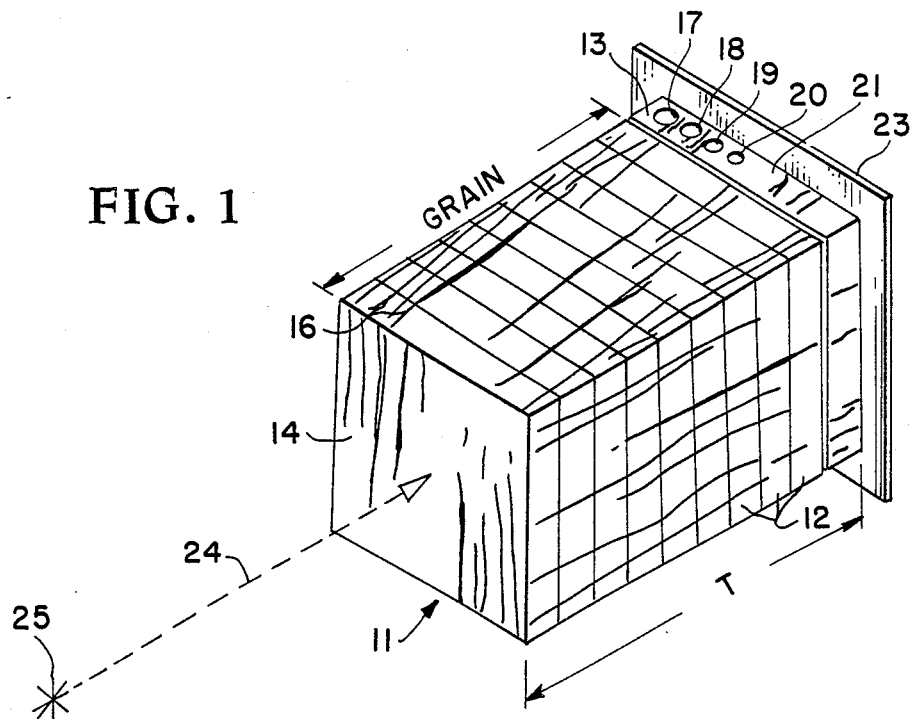
FIG. 1 is a perspective view illustrating a set-up for taking a radiographic film image of a wooden specimen having a plurality of test holes of varying diameters and depths therein.

Referring to the drawing FIG. 1 shows a demonstration set-p for practicing the preferred method of radiographic inspection of wooden members, in this instance, a 6-inch × 6-inch × 8-inch test specimen 11 of wood such as Sitka spruce (*Picea sitkensis*). While the specimen 11 is formed of nine 6-inch × by 6-inch by ¾ inch quarter-sawn pieces 12 and a single 6-inch × 6-inch by 1¼ inch quarter-sawn piece 13 that are clamped together, the specimen 11 may be formed of a solid piece of wood or wood-like material.

Figure 2:
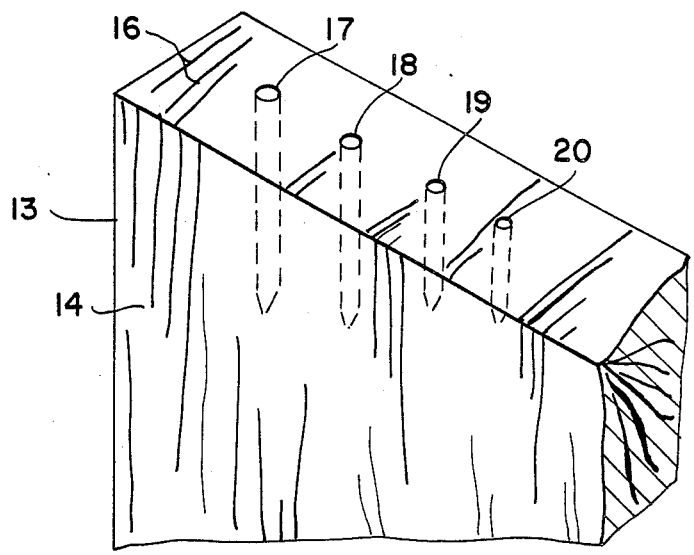
FIG. 2 is an enlarged, partial perspective of the wooden specimen shown in FIG. 1 illustrating the test holes in greater detail.

As shown in FIG. 2, grain lines 14 of the test specimen pieces 12 and 13 are spaced and generally parallel, running vertically in the front face of each and extending through the thickness of the specimen piece 13 as growth rings 16.

The piece 13 of specimen 11 is provided with four spaced and uniformly counter-bored test holes 17–20 in top edge 21. The test holes 17–20 are ⅛ inch, 3/32 inch, 1/16 inch and 0.040 inch in diameter, respectively, and extend parallel to varying depths into the test piece 13 and represent internal defects in the specimen 11 to be detected.

An x-ray film 23 positioned behind the test specimen 11 is exposed by a main beam of radiation 24 from a source 25 in a conventional x-ray machine such as a model SPX 160 made by Automation Industries, Danbury, Conn. The radiation beam 24 passes through the test specimen 11 tangentially to the grain lines 14, its intensity being determined by the thickness T of the test specimen 11, the distance between the radiation source 25 and the film 23, and the level of film exposure required to form the desired radiographic film images.

Figure 3:
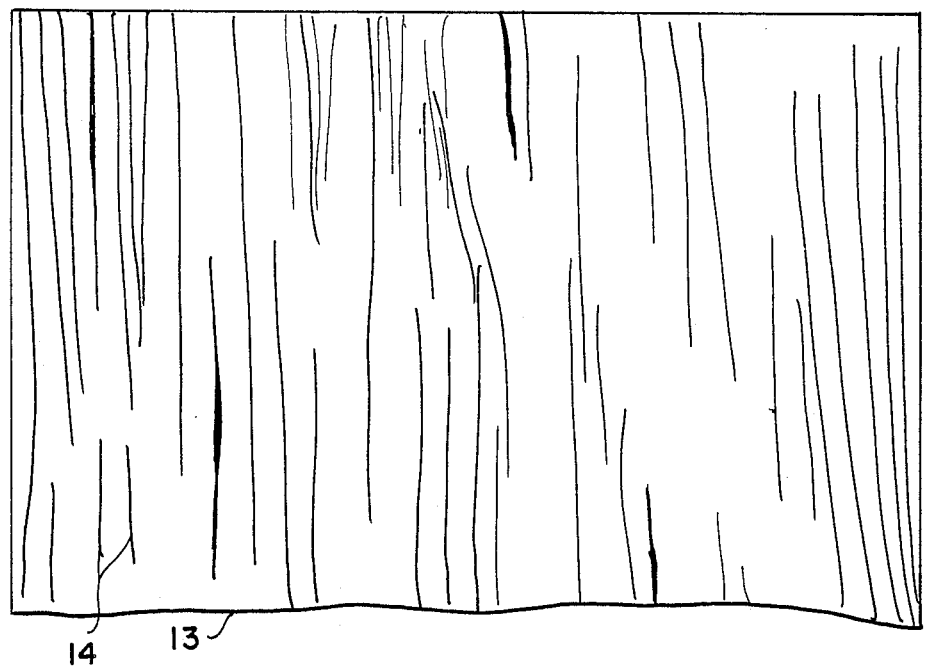
FIG. 3 is a plan view illustrating a "before" radiographic film image of the wooden specimen with test holes of varying diameters and depths therein as shown in FIG. 2.
Figure 4:
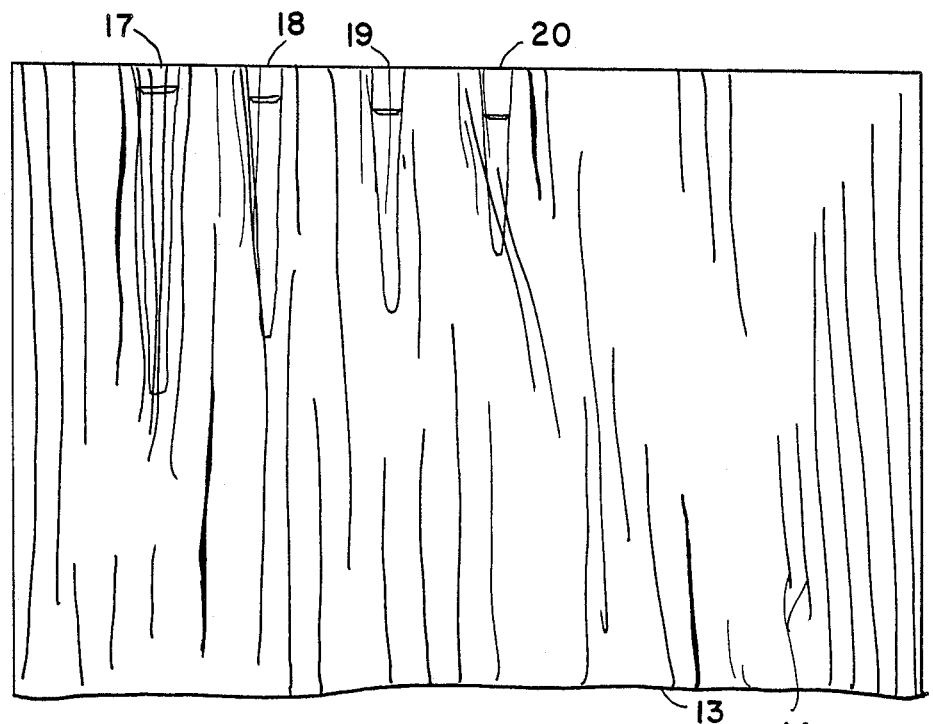
FIG. 4 is an identical plan view of a radiographic film image taken of the same wooden specimen "after" introducing a radiopaque penetrant into said test holes.

Referring to the drawings, FIGS. 3 and 4 illustrate identical radiographic film images taken through the test specimen 11 "before" and "after" the radiopaque penetrant is introduced into the test holes 17-20 in the piece 13.

The radiopaque penetrant may be introduced into the test holes 17-20 by means of flooding, gravity feed, capillary action or forced flow in sufficient quantity to fill the test holes and any internal defects, fissures, laminar separations, and voids opening into the test holes. As shown in FIG. 4, the test holes 17-20 are clearly visible in the "after" radiographic film image. This visual enhancement occurs because the radiopaque penetrant in the test holes in piece 13 absorb a greater portion of the radiation beam 24 to vary the exposure of the film 23 as compared to the film's exposure in the "before" radiograph. Since the radiopaque penetrant fills only the internal defects, the exposure of the remaining portions of the respective "before" and "after" radiographic films remains the same.

Radiographic sensitivity is the percentage of the diameter of the detected test hole to the thickness of the test specimen in which detected. Thus, as shown in FIG. 4, the use of radiopaque penetrant in accordance with this method detects all of the test holes 17-20 resulting in radiographic sensitivities of 1.56 percent, 1.17 percent, 0.78 percent, and 0.5 percent. This is in marked contrast to the "before" radiographic film image in which none of the test holes 17-20 are visible.

While FIGS. 1-4 illustrate the use of the method to detect test holes 17-20 in a test specimen 11, the method has been successfully used to reveal interlaminar shear cracks in sections of large laminated spruce wind tunnel fan blades up to twenty-eight inches in thickness that were radiographically invisible before the radiopaque penetrant was introduced in accordance with this invention. As noted the method is more effective when "before" and "after" radiographic film images are taken and compared.

Thus, the invention provides a safe, noncontaminating radiopaque penetrant for use in the radiographic inspection of wooden and wood-like materials, components, assemblies, and structures such as wooden aircraft components, fan and wind turbine blades, marine parts and insulators.

While a preferred method has been described in detail, numerous changes can be made within the principles of the invention which is to be limited only by the appended claims.

We claim:

1. A non-contaminating method of radiographic inspection of a wooden specimen comprising the steps of:
   introducing a non-contaminating, highly evaporative radiopaque penetrant formed of a fluorocarbon cleaning solvent into internal defects in said wooden specimen to be inspected through a surface opening therein;
   subjecting the wooden specimen to a beam of radiation sufficient to pass through said wooden specimen; and
   making a radiographic film image of said beam of radiation passing through said wooden specimen, said non-contaminating radiopaque penetrant in said internal defects within said specimen absorbing a portion of said beam of radiation passing therethrough, thereby enhancing the resulting film image of said internal defects without contaminating said wooden specimen.

2. The method of claim 1 including the steps of making a radiographic film image of said wooden specimen "before" introducing said radiopaque penetrant into said internal defects; and
   comparing said "before" radiographic film image with said radiographic film image made "after" introducing said radiopaque penetrant into said internal defects.

3. The method of claim 1 wherein said wooden specimen is quarter-sawn and said beam of radiation passes through said wooden specimen tangentially to the grain of said wooden specimens.

4. The method of claim 2 wherein said wooden specimen is quarter-sawn and said beam of radiation passes through said wooden specimen tangentially to the grain of said wooden specimen.

* * * * *